US012802555B2

(12) United States Patent
Schroder et al.

(10) Patent No.: US 12,802,555 B2
(45) Date of Patent: Nov. 17, 2026

(54) WIRELESS MOBILE DEVICE ACCESS TO NURSE CALL SYSTEM ALERTS AND DATA

(71) Applicant: Hill-Rom Services, Inc., Batesville, IN (US)

(72) Inventors: John S. Schroder, Apex, NC (US); James R. Price, Batesville, IN (US); Paul Hilburger, Pittsboro, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 18/978,038

(22) Filed: Dec. 12, 2024

(65) Prior Publication Data

US 2025/0218277 A1 Jul. 3, 2025

Related U.S. Application Data

(60) Provisional application No. 63/617,143, filed on Jan. 3, 2024.

(51) Int. Cl.
*G08B 26/00* (2006.01)
*G08B 21/02* (2006.01)
*G16H 40/67* (2018.01)

(52) U.S. Cl.
CPC ........... *G08B 26/008* (2013.01); *G08B 21/02* (2013.01); *G16H 40/67* (2018.01)

(58) Field of Classification Search
CPC ...... G08B 26/008; G08B 21/02; G16H 40/67; G16H 40/20
See application file for complete search history.

(56) References Cited

U.S. PATENT DOCUMENTS 5,319,355 A 6/1994 Russek
6,462,656 B2 10/2002 Ulrich et al.
(Continued)

FOREIGN PATENT DOCUMENTS

EP 3758026 A1 * 12/2020 ........... A61B 5/7275

OTHER PUBLICATIONS

Notification of Transmittal of the International Search Report and the Written Authority of the International Searching Authority, or the Declaration and Written Opinion of the International Searching Authority mailed by the United States Patent and Trademark Office as International Searching Authority for International Application No. PCT/US2024/060652; dated Mar. 3, 2025 (23 pages).
(Continued)

*Primary Examiner* — Omeed Alizada
(74) *Attorney, Agent, or Firm* — Barnes & Thornburg LLP

(57) ABSTRACT

A system, method, and tangible computer-readable storage media to link a nurse call system of a healthcare facility with a mobile phone, are provided. A nurse call server receives nurse calls, alerts, and device status data. A connected services architecture (CSA) is located at an entity geographically remote from the healthcare facility. The CSA has a proxy server to replicate the nurse calls, alerts, and device status data communicated to the proxy server from the nurse call server. A mobile application gateway is coupled to the nurse call server via a first path that excludes the proxy server and via a second path that includes the proxy server of the CSA. Wireless mobile devices of caregivers receive the nurse calls, alerts, and device status data from the mobile application gateway.

23 Claims, 8 Drawing Sheets

(56) References Cited

U.S. PATENT DOCUMENTS

| | | | |
|---|---|---|---|
| 7,319,386 | B2 | 1/2008 | Collins, Jr. et al. |
| 9,240,120 | B2 | 1/2016 | Girardeau et al. |
| 9,749,825 | B2 | 8/2017 | Payne et al. |
| 9,872,148 | B2 | 1/2018 | King et al. |
| 10,438,356 | B2 | 10/2019 | Dacosta |
| 11,257,588 | B2 | 2/2022 | Faulks et al. |
| 11,398,305 | B2 | 7/2022 | Girardeau et al. |
| 11,490,835 | B2 | 11/2022 | Durlach et al. |
| 11,504,071 | B2 | 11/2022 | Terry et al. |
| 11,672,442 | B2 | 6/2023 | Durlach et al. |
| 11,908,581 | B2 | 2/2024 | Kayser et al. |
| 2012/0078144 | A1 | 3/2012 | Sinykin |
| 2014/0266642 | A1 | 9/2014 | Girardeau et al. |
| 2016/0226825 | A1 * | 8/2016 | Ardeli ................. H04L 63/0254 |
| 2017/0262593 | A1 * | 9/2017 | Girardeau .............. G08B 25/10 |
| 2017/0287316 | A1 | 10/2017 | Wildman et al. |
| 2020/0155059 | A1 | 5/2020 | Kayser et al. |
| 2020/0211360 | A1 * | 7/2020 | Baker ................... G01S 13/878 |
| 2023/0014078 | A1 * | 1/2023 | Kayser ............. G06Q 10/06311 |
| 2023/0062727 | A1 * | 3/2023 | Etchison .............. A61B 5/0002 |
| 2023/0195866 | A1 * | 6/2023 | Hudgins ................. H04W 4/90 713/186 |
| 2023/0245770 | A1 * | 8/2023 | Ayers ................. G08B 13/1427 340/539.12 |
| 2023/0298740 | A1 | 9/2023 | Receveur et al. |
| 2024/0379218 | A1 | 11/2024 | Durlach et al. |

OTHER PUBLICATIONS

Instructions for Use Software Version 3.7 for Voalte One™; LAB01476 Rev 6; © 2020 (111 pages).

Instructions for Use Software Version 3.7 for Voalte Me™; LAB01477 Rev 5; © 2020 (92 pages).

* cited by examiner

WIRELESS MOBILE DEVICE ACCESS TO NURSE CALL SYSTEM ALERTS AND DATA

The present application claims the benefit, under 35 U.S.C. § 119(e), of U.S. Provisional Patent Application No. 63/617,143, filed Jan. 3, 2024, which is hereby incorporated by reference herein in its entirety.

BACKGROUND

The present disclosure relates to healthcare information systems and particularly, to healthcare information systems in which caregivers carry wireless mobile devices such as mobile phones. More particularly, the present disclosure relates to healthcare information systems having nurse call system connectivity to wireless mobile devices carried by caregivers.

Nurse call systems that send messages regarding nurse calls and alerts to wireless devices carried by caregivers are known. For example, the COMLINX® nurse call system, available from Hill-Rom Company, Inc., was operable to send nurse calls and alert messages to pagers carried by caregivers. See, for example, U.S. Pat. No. 6,462,656 in this regard. U.S. Pat. No. 5,319,355 also contemplates sending nurse calls to pagers carried by caregivers. U.S. Pat. No. 7,319,386 contemplates a system in which nurse calls and alerts are sent to various wireless communication devices such as pagers, VOCERA® badges, and telephone handsets, including ASCOM® or SPECTRALINK® handsets, via infrastructure located within a healthcare facility. U.S. Pat. No. 11,257,588 discloses a system of a healthcare facility in which nurse calls and alert messages are sent to touch screen based mobile phones of caregivers using infrastructure of the healthcare facility.

In the modern-day healthcare setting, caregivers oftentimes carry more sophisticated wireless mobile devices, such as mobile phones (aka "smart phones"), during their shifts. These more modern mobile phones are touch screen based and have a large amount of computing power for running a multitude of software applications. However, a full integration between nurse call systems and these types of modern day mobile phones, such as iOS™ and ANDROID™ mobile phones, has not yet been satisfactorily implemented. What is needed therefore, is a software application and/or an overall infrastructure system that makes the full scope of alert and status data resident in a nurse call system available on caregivers' wireless mobile devices, such as modern-day smart phones, while at the same time providing integration with other healthcare system and third party supplier functionality.

SUMMARY

An apparatus, system, or method may comprise one or more of the features recited in the appended claims and/or the following features which, alone or in any combination, may comprise patentable subject matter:

According to a first aspect of the present disclosure, a healthcare information system may include a nurse call server that may be located at a health care facility. The nurse call server may be configured to receive nurse calls, alerts, and device status data from devices that may be located in patient rooms of the healthcare facility. The devices that may be located in the patient rooms may include patient beds that support patients in the patient rooms. The healthcare information system of the first aspect may further include connected services architecture (CSA) that may be located at an entity geographically remote from the healthcare facility. The CSA may be communicatively coupled to the nurse call server and may have a proxy server configured to replicate the nurse calls, alerts, and device status data communicated to the proxy server from the nurse call server. The healthcare information system of the first aspect may also include a mobile application gateway that may be communicatively coupled to the nurse call server via a first path that may exclude the proxy server of the CSA and via a second path that may include the proxy server of the CSA. The healthcare information system of the first aspect still further may include wireless mobile devices that may be carried by caregivers in the healthcare facility and each wireless mobile device may be communicatively coupled with the mobile application gateway. Each wireless mobile device may be configured to receive the nurse calls, alerts, and device status data from the mobile application gateway.

In some embodiments, the healthcare information system of the first aspect further may include a master station computer and a status board that may be situated at a master nurse call station of a unit of the healthcare facility. The master station computer may be communicatively coupled to the nurse call server and to the status board. If desired, the status board may be configured to display, for each patient room in the unit, the associated nurse calls, alerts, and device status data. For example, the status board may be configured to display, for each patient room in the unit, risk information that may pertain to an associated patient in each of the patient rooms. The risk information also may be replicated in the proxy server of the CSA.

Optionally, the risk information may include a first icon that may indicate that the patient is a falls risk, a second icon that may indicate that the patient is a pulmonary risk, and a third icon that may indicate that the patient is at risk of developing pressure sores. Further optionally, each wireless mobile device may be configured to receive inputs from an associated caregiver to designate a corresponding patient with one or more of being a falls risk, being a pulmonary risk, and being at risk of developing pressure sores. Thus, each wireless mobile device may be configured to control the display of the risk information on the status board based on inputs that may be received from an associated caregiver to designate whether or not a corresponding patient has a particular risk.

The present disclosure further contemplates that each wireless mobile device may be configured to display a list of nurse calls and alerts for patients or patient rooms that may be assigned to the associated caregiver. If desired, the list of nurse calls and alerts may be sorted based on time since occurrence, with a most recent nurse call or alert being listed first. Optionally, the list may include, for each nurse call or alert, a field that may have the associated patient name, the associated room, a description of the associated type of nurse call or alert, and a time since the nurse call or alert occurred. Further optionally, the list may include, for each nurse call or alert, an icon indicative of the associated type of nurse call or alert. Still further optionally, the list may include, for each nurse call or alert, reminder information that may include at least one of the following: a rounding reminder if the associated caregiver is scheduled to make a round for the corresponding patient or a turn reminder if the associated caregiver is scheduled to turn the associated patient.

In some embodiments, the healthcare information system of the first aspect further may include graphical room stations that may be located in the patient rooms and that may be communicatively coupled to the nurse call server.

The graphical room stations may display reminder information that may pertain to tasks that are to be completed by caregivers for the patients in the respective rooms. In such embodiments, the wireless mobile devices may be configured to receive one or more inputs from the associated caregivers that may be indicative of completion of the tasks. For example, the reminder information may include rounding reminders and the one or more inputs may indicate that the associated caregiver has completed a round for a corresponding patient. As another example, the reminder information may include turn reminders and the one or more inputs may indicate that the associated caregiver has completed a turn of the corresponding patient.

As yet another example, the reminder information may include medication reminders and the one or more inputs may indicate that the associated caregiver has completed medication delivery to the corresponding patient. As still a further example, the reminder information may include patient temperature reminders and the one or more inputs may indicate that the associated caregiver has completed taking the corresponding patient's temperature. The present disclosure contemplates that selection of the one or more inputs by the caregivers to indicate completion of the tasks may be communicated to the nurse call server which may result in task lists for the caregivers being updated.

Optionally, the wireless mobile devices may be configured with an input that may summon housekeeping personnel to a selected patient room. Further optionally, the nurse call server may track caregiver performance metrics for each caregiver and the wireless mobile devices may be configured to display the caregiver performance metrics for the associated caregiver. For example, the caregiver performance metrics may include a time spent with each of the associated caregiver's assigned patients during a particular shift.

In some embodiments, the wireless mobile devices may be configured to display one or more call completion inputs that may be selectable by the associated caregiver to notify the nurse call server that a particular nurse call has been answered or that a particular alert condition has been rectified. Optionally, the healthcare information system of the first aspect further may include a locating system server that may be communicatively coupled to the nurse call server and that may receive locating data regarding locations of locating tags that may be worn by caregivers and/or that may be coupled to equipment in the healthcare facility. Further optionally, the locating data may be replicated in the proxy server of the CSA. Further optionally, each of the wireless mobile devices may be configured to display a floor plan of a portion of the healthcare facility and locations of caregivers and/or equipment may be shown on the floor plan based on the locating data. The present disclosure further contemplates that each of the wireless mobile devices may be configured to open a voice communication channel to a graphical room station that may be located in an associated patient room from which a corresponding nurse call originated.

According to a second aspect of the present disclosure, a method may include receiving at a nurse call server that may be located at a health care facility, nurse calls, alerts, and device status data from devices that may be located in patient rooms of the healthcare facility. The devices that may be located in the patient rooms may include patient beds that support patients in the patient rooms. The method of the second aspect further may include replicating the nurse calls, alerts, and bed status data at a proxy server of connected services architecture (CSA) that may be located at an entity geographically remote from the healthcare facility. The CSA may be communicatively coupled to the nurse call server. The method of the second aspect also may include communicating between the nurse call server and a mobile application gateway via a first path that may exclude the proxy server of the CSA and via a second path that may include the proxy server of the CSA. The method of the second aspect still further may include receiving at wireless mobile devices that may be carried by caregivers in the healthcare facility, the nurse calls, alerts, and device status data that may be transmitted from the mobile application gateway.

In some embodiments, the method of the second aspect further may include receiving at a master station computer that may be situated at a master nurse call station of a unit of the healthcare facility, the nurse calls, alerts, and bed status data, and displaying, for each patient room in the unit, the associated nurse calls, alerts, and device status data on a status board that may be located at the master nurse call station and that may be communicatively coupled to the master station computer. Optionally, the method of the second aspect further may include displaying on the status board, for each patient room in the unit, risk information that may pertain to an associated patient in each of the patient rooms and replicating the risk information at the proxy server of the CSA.

If desired, the risk information of the method of the second aspect may include a first icon that may indicate that the patient is a falls risk, a second icon that may indicate that the patient is a pulmonary risk, and a third icon that may indicate that the patient is at risk of developing pressure sores. The present disclosure further contemplates that the method of the second aspect further may include configuring each wireless mobile device to receive inputs from an associated caregiver to designate a corresponding patient with one or more of being a falls risk, being a pulmonary risk, and being at risk of developing pressure sores. Optionally, the method of the second aspect further may include configuring each wireless mobile device to control the display of the risk information on the status board based on inputs that may be received from an associated caregiver to designate whether or not a corresponding patient has a particular risk.

In some embodiments, the method of the second aspect further includes configuring each wireless mobile device to display a list of nurse calls and alerts for patients or patient rooms that may be assigned to the associated caregiver. If desired, the list of nurse calls and alerts of the second aspect may be sorted based on time since occurrence, with a most recent nurse call or alert being listed first. Optionally, the list of the second aspect may include, for each nurse call or alert, a field that may include the associated patient name, the associated room, a description of the associated type of nurse call or alert, and a time since the nurse call or alert occurred. Further optionally, the list may include, for each nurse call or alert, an icon that may be indicative of the associated type of nurse call or alert.

If desired, the list may include, for each nurse call or alert, reminder information that may include at least one of the following: a rounding reminder if the associated caregiver is scheduled to make a round for the corresponding patient or a turn reminder if the associated caregiver is scheduled to turn the associated patient. The method of the second aspect further may include providing graphical room stations in the patient rooms, communicatively coupling the graphical room stations to the nurse call server, displaying on the graphical room stations reminder information pertaining to tasks that are to be completed by caregivers for the patients in the respective rooms, and configuring the wireless mobile devices to receive one or more inputs from the associated caregivers that may be indicative of completion of the tasks.

Optionally, the reminder information of the second aspect may include rounding reminders and the one or more inputs may indicate that the associated caregiver has completed a round for a corresponding patient. As another example, the reminder information of the second aspect may include turn reminders and the one or more inputs may indicate that the associated caregiver has completed a turn of the corresponding patient. As a further example, the reminder information of the second aspect may include medication reminders and the one or more inputs may indicate that the associated caregiver has completed medication delivery to the corresponding patient. As still another example, the reminder information of the second aspect may include patient temperature reminders and the one or more inputs may indicate that the associated caregiver has completed taking the corresponding patient's temperature.

In some embodiments, the method of the second aspect further may include communicating the selection of the one or more inputs by the caregivers that may indicate completion of the tasks to the nurse call server and updating the task lists for the caregivers in the nurse call server. If desired, the method of the second aspect further may include configuring the wireless mobile devices with an input to summon housekeeping personnel to a selected patient room. Also, if desired, the method of the second aspect further may include tracking with the nurse call server caregiver performance metrics for each caregiver and configuring the wireless mobile devices to display the caregiver performance metrics for the associated caregiver. For example, the caregiver performance metrics of the second aspect may include a time spent with each of the associated caregiver's assigned patients during a particular shift.

Optionally, the method of the second aspect further may include configuring the wireless mobile devices to display one or more call completion inputs that may be selectable by the associated caregiver to notify the nurse call server that a particular nurse call has been answered or that a particular alert condition has been rectified. Further optionally, the method of the second aspect further may include providing a locating system server that may be communicatively coupled to the nurse call server, receiving locating data regarding locations of locating tags that may be worn by caregivers and/or that may be coupled to equipment in the healthcare facility, and replicating the locating data in the proxy server of the CSA.

If desired, the method of the second aspect further may include configuring the wireless mobile device to display a floor plan of a portion of the healthcare facility and showing locations of caregivers and/or equipment on the floor plan based on the locating data. Also if desired, the method of the second aspect further may include configuring each of the wireless mobile devices to open a voice communication channel to a graphical room station located in an associated patient room from which a corresponding nurse call originated.

According to a third aspect of the present disclosure, one or more tangible computer-readable storage media may include a plurality of instructions that, when executed, may cause a wireless mobile device to receive nurse calls, alerts, and device status data that may been received initially at a nurse call server that may be located at a health care facility, that may be replicated at a proxy server of connected services architecture (CSA) that may be located at an entity geographically remote from the healthcare facility, and that may have been communicated from the nurse call server to a mobile application gateway via a first path that may exclude the proxy server of the CSA and via a second path that may include the proxy server of the CSA.

In some embodiments of the one or more tangible computer-readable storage media of the third aspect, the plurality of instructions further may cause the wireless mobile device to display the nurse calls, alerts, and bed status data, for each patient room in a unit of the healthcare facility. Optionally, the plurality of instructions further may cause the wireless mobile device to display, for each patient room in the unit, risk information that may pertain to an associated patient in each of the patient rooms. Further optionally, the plurality of instructions further may cause the wireless mobile device to be configured to receive inputs from an associated caregiver to designate a corresponding patient with one or more of being a falls risk, being a pulmonary risk, and being at risk of developing pressure sores.

If desired, the plurality of instructions further may cause the wireless mobile device to be configured to transmit messages that may indicate whether the corresponding patient has been designated as one or more of being a falls risk, being a pulmonary risk, and being at risk of developing pressure sores so that the risk information input on the wireless mobile device can be updated on a status board. Also, if desired, the plurality of instructions further may cause the wireless mobile device to be configured to display a list of nurse calls and alerts for patients or patient rooms that may be assigned to a caregiver that may be associated with the wireless mobile device.

Optionally, the list of nurse calls and alerts of the third aspect may be sorted based on time since occurrence, with a most recent nurse call or alert being listed first. Further optionally, the list of the third aspect may include, for each nurse call or alert, a field that may include the associated patient name, the associated room, a description of the associated type of nurse call or alert, and a time since the nurse call or alert occurred. Still further optionally, the list may include, for each nurse call or alert, an icon that may be indicative of the associated type of nurse call or alert. Yet further optionally, the list of the third aspect may include, for each nurse call or alert, reminder information that may include at least one of the following: a rounding reminder if the associated caregiver is scheduled to make a round for the corresponding patient or a turn reminder if the associated caregiver is scheduled to turn the associated patient.

In some embodiments, the plurality of instructions of the third aspect further may cause the wireless mobile device to be configured to: display tasks that are to be completed for one or more patients by a caregiver associated with the wireless mobile device, receive inputs indicating that one or more of the tasks may have been completed, and transmit messages that may indicate that the one or more tasks may have been completed so that task information displayed on graphical room stations in a corresponding patient rooms can be updated.

The present disclosure contemplates that at least one of the messages of the third aspect may be transmitted by the wireless mobile device in response to at least one of the inputs indicating that the associated caregiver has completed a round for a corresponding patient. As another example, at least one of the messages of the third aspect may be transmitted by the wireless mobile device in response to at least one of the inputs indicating that the associated caregiver has completed a turn of a corresponding patient. As a further example, at least one of the messages of the third aspect may be transmitted by the wireless mobile device in response to at least one of the inputs indicating that the associated caregiver has completed medication delivery to a corresponding patient. As yet another example, at least one of the messages of the third aspect may be transmitted by the wireless mobile device in response to the at least one input indicating that the associated caregiver has completed taking a corresponding patient's temperature.

In some embodiments of the third aspect, the plurality of instructions further may cause the wireless mobile device to be configured to: display tasks that are to be completed for one or more patients by a caregiver associated with the wireless mobile device, receive inputs indicating that one or more of the tasks have been completed, and transmit messages indicating that the one or more tasks have been completed so that task information stored in the nurse call server can be updated. If desired, the plurality of instructions further may cause the wireless mobile device to display an input that may be selectable to summon housekeeping personnel to a designated patient room.

Optionally, the plurality of instructions of the third aspect further may cause the wireless mobile device to display caregiver performance metrics for an associated caregiver. For example, the caregiver performance metrics of the third aspect may comprise a time spent with each of the associated caregiver's assigned patients during a particular shift. Further optionally, the plurality of instructions of the third aspect further may cause the wireless mobile device to display one or more call completion inputs that may be selectable by an associated caregiver to notify the nurse call server that a particular nurse call has been answered or that a particular alert condition has been rectified.

If desired, the plurality of instructions of the third aspect further may cause the wireless mobile device to be configured to communicate with a locating system server that may be communicatively coupled to the nurse call server and that may receive locating data regarding locations of locating tags that may be worn by caregivers and/or that may be coupled to equipment in the healthcare facility. Also, if desired, the plurality of instructions of the third aspect further may cause the wireless mobile device to display a floor plan of a portion of the healthcare facility and to show locations of caregivers and/or equipment on the floor plan based on the locating data. Further if desired, the plurality of instructions of the third aspect further may cause the wireless mobile device to be configured to open a voice communication channel to a graphical room station that may be located in an associated patient room from which a corresponding nurse call originated.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
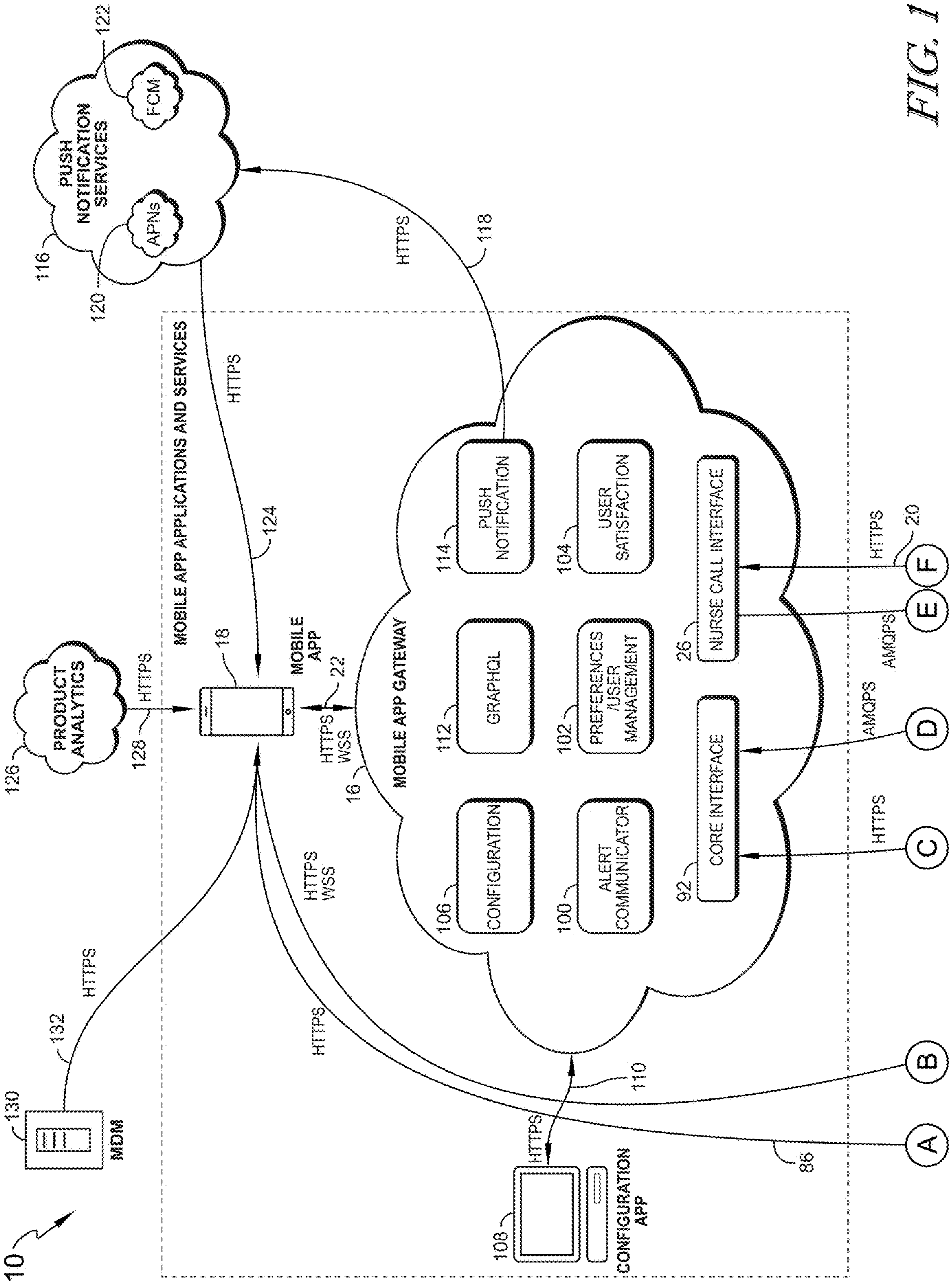
FIG. 1 is a block diagram of a healthcare information system in which a nurse call system is communicatively coupled to connected service architecture (CSA), which in turn is connected to a mobile app gateway which is coupled to a mobile phone, the nurse call system also being communicatively coupled to the mobile app gateway via a path that excludes the CSA.
Figure 1:
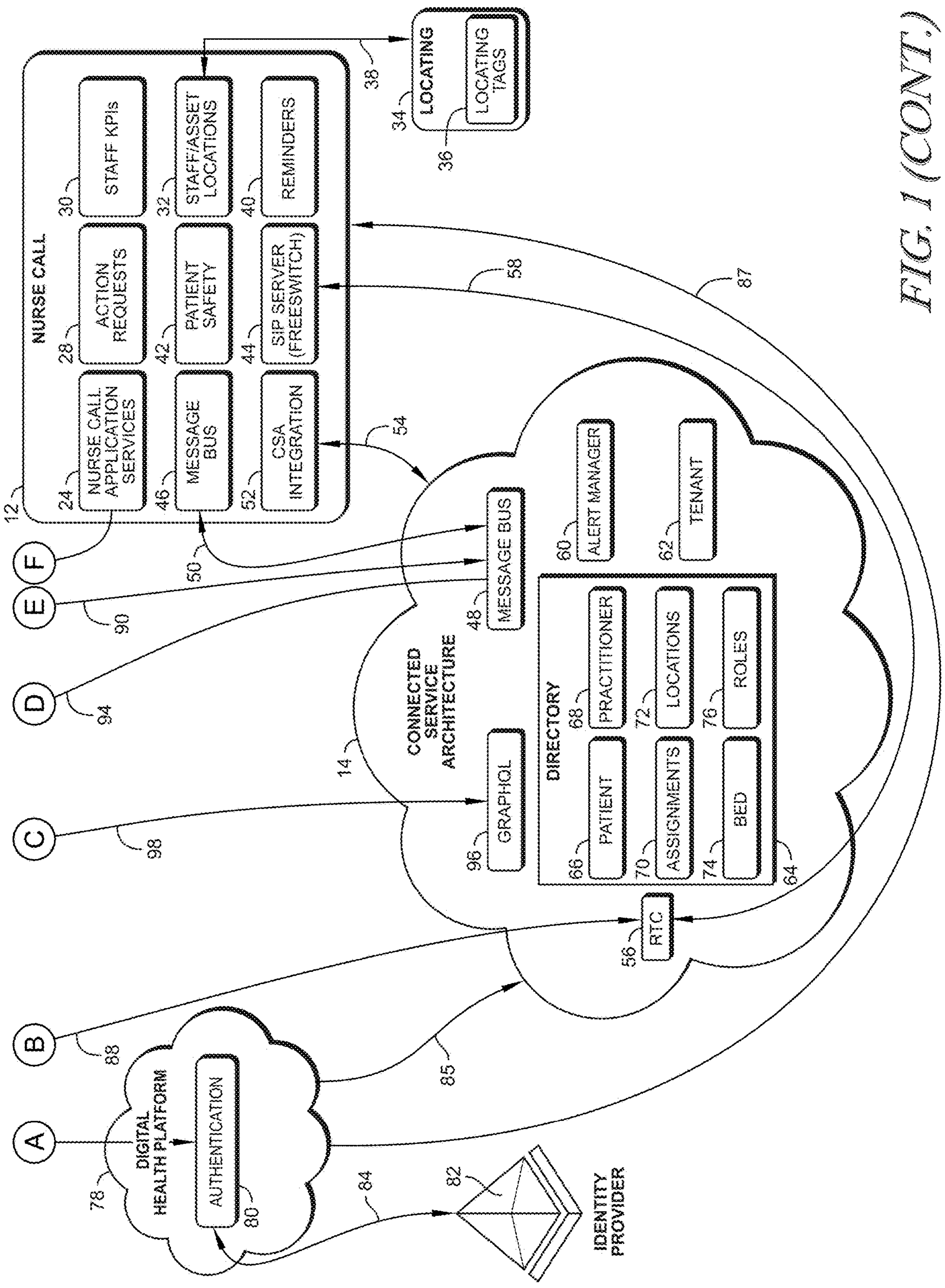

A healthcare information system 10 according to the present disclosure includes a nurse call system 12 that is communicatively coupled to connected service architecture (CSA) 14 which is, in turn, communicatively coupled to a mobile app gateway 16 as shown in FIG. 1. Mobile app gateway 16 is communicatively coupled to a plurality of wireless mobile devices, illustratively mobile phones 18, that are carried by caregivers in a health care facility but only one mobile phone 18 is illustrated in FIG. 1 for the sake of economy of illustration. Each mobile phone 18 receives alerts, nurse calls, and other messages from nurse call system 12 via first path that includes the CSA 14 and via a second path that excludes the CSA 14.

Still referring to FIG. 1, nurse call system 12 communicates with mobile app gateway 16 by way of a hypertext transfer protocol secure (HTTPS) link or infrastructure 20. The HTTPS link sends encrypted messages from nurse call system 12 to mobile app gateway 16 which, in turn, sends encrypted messages by way of HTTPS WebSocket Secure (wss) links or infrastructure 22 to mobile phones 18 assigned to the rooms or patients from which the messages originated. More particularly, a nurse call application services portion 24 of nurse call system 12 communicates via link 20 with a nurse call interface 26 of mobile app gateway.

Nurse call system 12 also includes applications or services for handling action requests 28 which are preconfigured calls that caregivers can use to alert other staff of situations that require their attention; staff key performance indicators (KPI's) 30 which are metrics calculated for staff as it pertains to their job duties; and staff/asset locations 32 which involves receiving location data from a locating system 34 to determine the whereabouts of staff and assets within the healthcare facility. The locating system 34 includes locating tags 36 that are worn by caregivers and other staff and/or that are attached to equipment so that locating data transmitted from the tags and received by receivers at fixed locations in the healthcare facility can be mapped to locations by a locating server of the locating system 34. The locating system 34 and nurse call system are communicatively coupled by an Ethernet link or infrastructure 38.

Further applications or services of nurse call system 12 include reminders 40 which is a microservice that manages nurse call reminders such as rounding, turns due, medication due, temperature check due, and the like; and patient safety 42 which is a microservice that monitors nurse call states and generates alerts pertaining to patient safety. Such patient safety alerts include, for example, one or more bed siderails being lowered, a patient getting out of bed or moving toward getting out of bed, an upper frame of a patient bed being moved out of lowest position, and bed caster brakes being unbraked. Another application or service of nurse call system 12 is a session initiation protocol (SIP) server application 44 which is a service that manages voice communications between staff and patients or between staff members. In some embodiments, the SIP server application 44 uses FREESWITCH™ open source software.

Nurse call system 12 also includes a message bus service or application 46 which is an event bus used to announce changes of interest to subscribing clients and is used for asynchronous passing of messages between service applications. Message bus 46 of nurse call system 12 is communicatively coupled to a message bus 48 of the CSA 14 by way of a bidirectional communication link or infrastructure 50. Nurse call system 12 further includes a CSA integration service 52 which synchronizes nurse call data with the CSA 14. This enables the CSA 14 to replicate the nurse call data within a proxy server of the CSA 14. CSA integration service 52 is communicatively coupled to the CSA 14 by way of a bidirectional communication link 54. In general, each of the applications or services of nurse call system 12 are executed in software stored in memory of one or more nurse call servers of nurse call system 12.

In addition to message bus 48, CSA 14 has applications or services including a real-time communications (RTC) service 56 which enables voice and chat communications and that is communicatively coupled to SIP server application 44 by way of a bidirectional communication link 58; an alert manager 60 which is a service that handles alerts according to the Integrating the Healthcare Enterprise (IHE) protocol and routes the IHE alerts to the intended recipients; and a tenant service 62 which is a service responsible for managing information between multiple customer locations. CSA 14 also has a directory 64 which, in turn, has sub-directories for patients 66 (e.g., data pertaining to patient name, date of birth, risks, etc.), practitioners 68 (e.g., data to caregivers and other staff), assignments 70 (e.g., mapping between staff, patients, roles, and wireless devices 18), locations 72 (e.g., organizational units, such as division, campus, nursing units, and rooms configured for a healthcare facility); beds 74 (e.g., data pertaining to patient beds); and roles 76 (e.g., job functions that are assigned to practitioners).

With continued reference to FIG. 1, system 10 further includes a digital health platform 78, such as the Baxter Digital Health Platform available from Baxter International Inc. of Deerfield, Illinois, U.S.A. Digital health platform 78 includes an authentication application or service 80 which is responsible for authenticating login clients by verifying credentials against an identity provider 82 which is communicatively coupled to authentication application 80 via a bidirectional communication link 84. Authentication application 80 is also communicatively coupled to each mobile phone 18 by way of bidirectional HTTPS links or infrastructure 86. Additionally, in the illustrative example, digital health platform 78 is communicatively coupled to CSA 14 by a unidirectional communication link 85 and to nurse call system 12 by a unidirectional communication link 87. CSA 14 and digital health platform 78 are located geographically distant from the healthcare facility at one or more third party facilities in the illustrative example.

Referring once again to CSA 14, the RTC service 56 is communicatively coupled to each mobile phone 18 by way of bidirectional HTTPS wss links or infrastructure 88. As shown in FIG. 1, nurse call interface 26 of mobile app gateway 16 is communicatively coupled to message bus 48 of CSA 14 by way of an Advanced Message Queuing Protocol Secure (AMPQS) link or infrastructure 90. Furthermore, message bus 48 of CSA 14 is communicatively coupled to a core interface 92 by another AMPQS link or infrastructure 94. Links 90, 94 are unidirectional in that link 90 has messages going from nurse call interface 26 of mobile app gateway 16 to message bus 48 of CSA 14 whereas link 94 has messages going from message bus 48 of CSA 14 to core interface 92 of mobile app gateway 16. CSA 14 further has a GRAPHQL™ application or service 96 which is communicatively coupled to core interface 92 of mobile app gateway 16 via a bidirectional HTTPS link or infrastructure 98. GRAPHQL™ application 96 enables mobile app gateway 16 to access the CSA services using an open source query language protocol. In general, each of the applications or services of CSA 14 are executed in software stored in memory of one or more CSA servers of CSA 14.

Still referring to FIG. 1, mobile app gateway 16 includes an alert communicator application or service 100 which is a service that receives IHE alert dissemination messages from the alert manager 60 of CSA 14 and sends dissemination alert status messages to the alert manager 60. The alert communicator service 100 also forwards and receives dissemination alert status messages to and from the mobile phones 18. Mobile app gateway 16 also has a preferences/user management application or service 102 in which preferences are settings for the mobile applications of the various mobile phones 18 of caregivers and other staff that are configured for logged-in staff and in which user management handles the login process and manages authentication and authorization. Mobile app gateway 16 further includes a user satisfaction application or service 104 which is a microservice responsible for managing data collected from user (e.g., caregivers and other staff) feedback.

Mobile app gateway 16 includes a configuration service or application which is a web application used to configure settings for the mobile application of each mobile phone 18. In this regard a configuration computer 108 is coupled to mobile app gateway 16 by way of a bidirectional HTTPS link or infrastructure 110 and executes another configuration application to enable a user, such as an administrator, to configure the settings for the mobile application of mobile phone 18. Mobile app gateway 16 also includes a GRAPHQL™ service or application 112 that is used to send GRAPHQL open source query language messages to CSA 14. Illustrative mobile app gateway 16 additionally has a push notification service or application 114 which is a microservice used to initiate push notification requests to each mobile phone, which may be an iOS™ or ANDROID™ mobile device, for example. In general, each of the applications or services of mobile app gateway 16 are executed in software stored in memory of one or more gateway servers of mobile app gateway 16. Mobile app gateway 16 is located at a healthcare facility in some embodiments and is located geographically distant from the healthcare facility at a third party facility in other embodiments.

Push notifications are sent from service 114 of mobile app gateway to a push notification server 116 via a unidirectional HTTPS link or infrastructure 118. Push notification server 116 has software for implementing APPLE™ push notifications (APNs) 120 and FIREBASE™ cloud messaging (FCM) 122. APNs 120 are the only currently available means of delivering asynchronous events to an iOS-based application and FCM 122 is the only currently available means of delivering asynchronous events to an ANDROID-based application. APNs 120 and FCM 122 are used to wake the mobile application of the mobile phones 18 as part of the initiation of voice communication over SIP in addition to event notifications related to alert request status and other events. Push notification server 116 is communicatively coupled to each mobile phone 18 via unidirectional HTTPS links or infrastructure 124.

As shown in FIG. 1, system 10 optionally may include one or more products analytics servers 126 which implements a third party service that is used to track users' interactions with the mobile applications of the mobile phones such as screen views, button clicks, usage of other user inputs, etc. Server 126 communicates with the mobile phones 18 by way of HTTPS links or infrastructure 128. Illustrative system 10 further includes one or more mobile device management (MDM) servers 130 which are locally hosted systems at healthcare facilities and which are used to provide a reference version of the mobile application for mobile phones 18 along with configuration information required for use of mobile phones 18 in the facility. Configuration information includes, for example, the server and port associated with the reverse proxy. The one or more MDM servers 130 communicate with mobile phones 18 by way of unidirectional HTTPS links or infrastructure 132.

Figure 2:
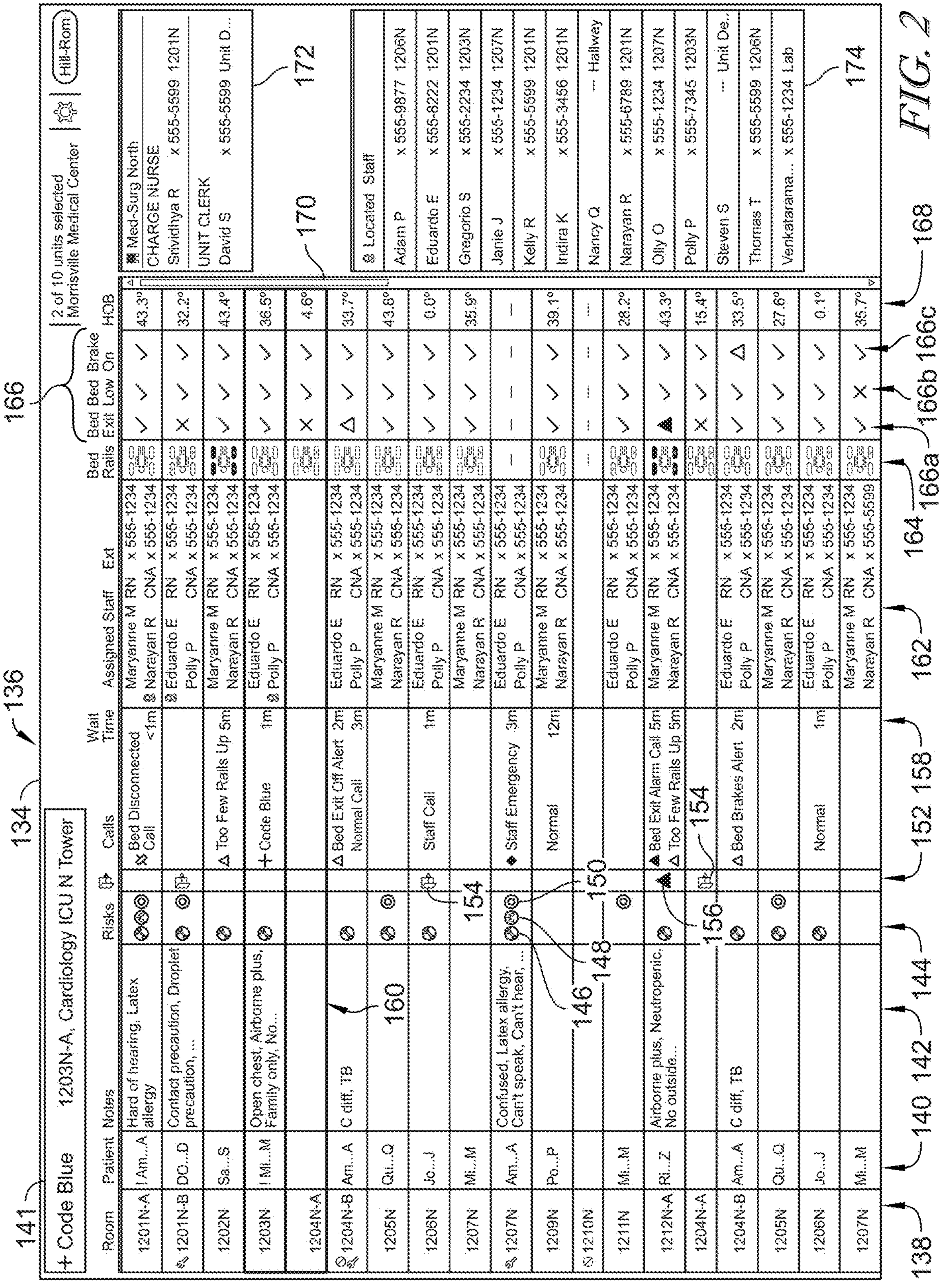
FIG. 2 is a screen shot of a status board located at a master nurse call station showing the status board displaying a wide variety of alert and device status data that originate from patient rooms.

Referring now to FIG. 2, an example of a screen shot 134 of a status board 136 which is included as part of nurse call system 12 and located at a master nurse call station of a unit of the healthcare facility. The status board 136 is communicatively coupled so a master nurse call computer and displays a wide variety of alert and device status data that originate from patient rooms of the healthcare facility. It should be appreciated that status board 136 is a large display screen on the order of 3 feet to 6 feet in diagonal, or more, and that is typically mounted at the master nurse station on a wall so as to be viewable by all staff members that are in close proximity to the master nurse station.

Going from left to right in FIG. 2, screen shot 134 includes a room column 138 which shows the room numbers of the various rooms in the unit associated with the status board 136 and a patient column 140 showing, in a Health Insurance Portability and Accountability Act (HIPAA) compliant format, the names of the patients in the various rooms. The HIPAA compliant format is, for each patient, the first two letters of the patient's last name, a set of ellipses, and the first letter of the patient's first name (e.g., in the last row of screen shot 134, the patient's name is shown as "Mi . . . M"). A header block 141 at the top of screen shot 134 indicates that the unit associated with status board 136 is "Cardiology ICU N Tower."

Continuing from left to right in FIG. 2, screen shot 134 includes a notes column 142 which shows notes that caregivers have entered about various patients. Examples of some of the notes in screen shot 134 include, "Hard of hearing, Latex allergy;" "Contact precaution, droplet precaution;" "Open chest, Airborne plus, Family only, No . . . ;" "C diff, TB;" "Confused, Latex allergy, Can't speak, Can't hear;" and "Neutropenic, No outside . . . ." Thus, while the notes may include anything caregivers have entered about the patient, it can be seen from the illustrative examples that the notes generally relate to the corresponding patient's medical conditions, physical limitations, allergies, contagion risk, and visitor limitations.

The next column in FIG. 2 is a risks column 144 which has icons to indicate a corresponding patient's medical risks. Up to three icons can be shown in column 144 for each patient in the illustrative embodiment. More particularly, in the illustrative example, the three icons includes a falls risk icon 146 to indicate that the corresponding patient is a falls risk, a pulmonary risk icon 148 to indicate that the corresponding patient is at risk of developing pulmonary complications such as ventilated assisted pneumonia (VAP), and a skin risk icon 150 to indicate that the corresponding patient is at risk of developing pressure ulcers (aka bed sores or decubitus ulcers).

To the right of column 144 in screen shot 134 is an out-of-room column 152 that includes an out of room icon 154 if a corresponding patient has left their patient room, such as for therapy, x-rays, etc. or to be discharged from the healthcare facility. Column 152 also includes a bed exit alarm call icon 156 if the corresponding patient has gotten out of bed when the patient position monitoring (PPM)/bed exit system of the associated patient bed has been armed (e.g., turned on) to monitor for patient bed exit or movement toward bed exit.

The next column in screen shot 134 of status board 136 is a calls column 158 which shows all the active calls for the various patient rooms and also shows the wait time, in minutes, subsequent to the occurrence of the respective call. Such calls in column 158 are based on alerts or alarms from equipment in the room, such as the patient beds, or based on a patient pressing a nurse call button on the corresponding patient bed or a pillow speaker unit or based on a caregiver or other staff action in the patient room. For example, in row four 160 of screen shot 134, a caregiver has pulled a code blue lever on a room station (e.g., a GRS or a standard room station) in the corresponding patient room and a "+ Code Blue" message appears in column 158. This same message appears in header block 141 along with the room "1203N-A" corresponding to the room in which the code blue is occurring. The term "code blue" means that the corresponding patient has gone into respiratory or cardiac arrest and likely requires cardiopulmonary resuscitation (CPR).

In the illustrative example of FIG. 2, other calls appearing in column 158 include the following: "Bed Disconnected Call" to indicate that the patient bed in the corresponding room has become unplugged from power or from the nurse call system 12; "Too Few Rails Up" to indicate that one or more siderails of the patient bed have been lowered for a patient who is a falls risk, for example; "Bed Exit Off Alert" to indicate that the PPM/bed exit system of a patient bed in a room of a patient who is a falls risk has been disarmed (or turned off so as not to monitor the patient's position or bed exit); "Normal" to indicate that the patient has pressed a nurse call button to speak with or summon a caregiver; "Staff Call" to indicate that a staff member in a particular patient room is placing a call to another staff member using a room station, a badge or tag with communication capability, or the associated mobile phone 18; "Staff Emergency" to indicate that one staff member has placed an emergency call using a staff locating tag/badge, or using a room station to summon one or more other staff members, or using the associated mobile phone 18 to summon one or more other staff members; "Bed Exit Alarm Call" to indicate the corresponding patient has gotten out of bed when the patient PPM/bed exit system of the associated patient bed has been armed (e.g., turned on) to monitor for patient bed exit or movement toward bed exit; and "Bed Brakes Alert" to indicate that caster brakes of the corresponding patient bed have been unbraked or released.

Continuing from left to right in FIG. 2, an assigned staff column 162 shows the staff members who are assigned to each of the patient rooms in the unit. In the illustrative example, there are two staff members (e.g., caregivers) assigned to each patient room. The format for showing the assigned caregivers in column 162 is full first name followed by first letter of last name. To the right of the name designation in column 162 is a role designator, typically an acronym, for each staff member. In the illustrative example of FIG. 2, the role designators include "RN" for registered nurse and "CNA" for certified nursing assistant. To the right of the role designators in column 162 are the phone numbers or extensions for each staff member, which are the phone numbers of the associated mobile phones 18 in some embodiments.

The next column of screen shot 134 of status board 136 is a bed rails column 164 that shows a patient and bed siderails icon with color coding to indicate the status of the siderails of each patient bed in each of the corresponding patient rooms. The icon is a simplified view from above the patient such that four line segments around the patient icon portion are representative of the four bed siderails. The patient icon portion has a small circle indicative of the patient's head such that the two line segments adjacent the small circle of the patient icon portion represent the head end siderails of the corresponding patient bed and the other two line segments are the foot end siderails of the corresponding patient bed.

With regard to the color coding of the icons appearing in column 164 for siderail status, green indicates that the corresponding siderail is in a raised position inhibiting patient exit from the respective bed; yellow indicates that the corresponding siderail is lowered but does not result in an alert or alarm condition, such as if a caregiver is in the patient room and has assisted the patient in getting out of bed or the PPM/bed exit system is not armed such that patient position and bed exit is not being monitored, or if no patient is assigned to the corresponding bed; and red indicates that the corresponding siderail is lowered and results in an alarm condition which, in turn, results in a call being placed and appearing in calls column 158. The patient portion of the icons appearing in column 164 is also color coded such that green indicates that a patient is sensed to be in the corresponding patient bed and gray indicates that no patient is sensed to be in the corresponding patient bed.

To the right of column 164 in screen shot 134 is a bed status column 166 which includes three sub-portions including sub-portion 166*a* to indicate bed exit status for each patient bed in the corresponding unit, sub-portion 166*b* to indicate bed low status for each patient bed in the corresponding unit, and sub-portion 166*c* to indicate brake on status for each patient bed in the corresponding unit. In sub-portion 166*a* of column 166 a check mark means the PPM/bed exit system is armed; an X mark means that the PPM/bed exit system is not armed; an empty triangle means the PPM/bed exit system it not armed but should be for a falls risk patient, or that a patient is absent from the room or not assigned to the room; a dash indicates that no patient bed is currently transmitting bed status data from the corresponding room; and a filled in triangle means that the PPM/bed exit system is armed and is alarming because the corresponding patient has exited the bed or has moved toward exiting the bed by a threshold amount (e.g., depending the mode of the PPM/bed exit system).

With regard to sub-portion 166*b* of column 166, a check mark means that an upper frame of the corresponding bed is in its low position, an X mark means the upper frame of the corresponding bed is not in its low position, and a dash indicates that no patient bed is currently transmitting bed status data from the corresponding room. With regard to sub-portion 166*c* of column 166, a check mark means that casters brakes of the corresponding bed are braked (e.g., locked or "on"), an X mark (not shown in FIG. 2) means that the caster brakes of the corresponding bed are unbraked (e.g., unlocked or "off"), an empty triangle means that a bed brakes alert is occurring such as for a corresponding falls risk patient, and a dash indicates that no patient bed is currently transmitting bed status data from the corresponding room.

To the right of bed status column 166 is a head of bed (HOB) column 168 that contains an angle at which a head section of the corresponding bed is raised relative to the upper frame of the corresponding bed or relative to horizontal depending upon the type of angle sensor used (e.g., potentiometer or accelerometer). Some patient beds permit a HOB alarm to be turned on which results in an alarm being sent if the HOB angle drops below a threshold angle, such as 30 or 45 degrees, for example. In such patient beds, a HOB alarm message appears in calls column 158 for the corresponding bed. To the right of HOB column 168, a scroll bar 170 and is movable vertically to reveal additional patient rooms and patients in the unit along with corresponding information of the type just discussed with regard to screen shot 134 of FIG. 2.

Still referring to FIG. 2, screen shot 134 of status board 136 includes a first window 172 that lists the names, phone number, and location of a charge nurse and a unit clerk for the associated unit. Beneath first window 172 is a second window 174 that lists the names, phone numbers, and locations of the located staff of the unit. The locations shown in windows 172, 174 are based on information transmitted to nurse call system 12 from locating system 34. The names shown in windows 172, 174 are in the same format as the names shown in assigned staff column 162. That is, full first name followed by first letter of last name. In some embodiments, the phone numbers shown in windows 172, 174 are the phone numbers of mobile phones 18 that are carried by caregivers and other staff.

Figure 3:
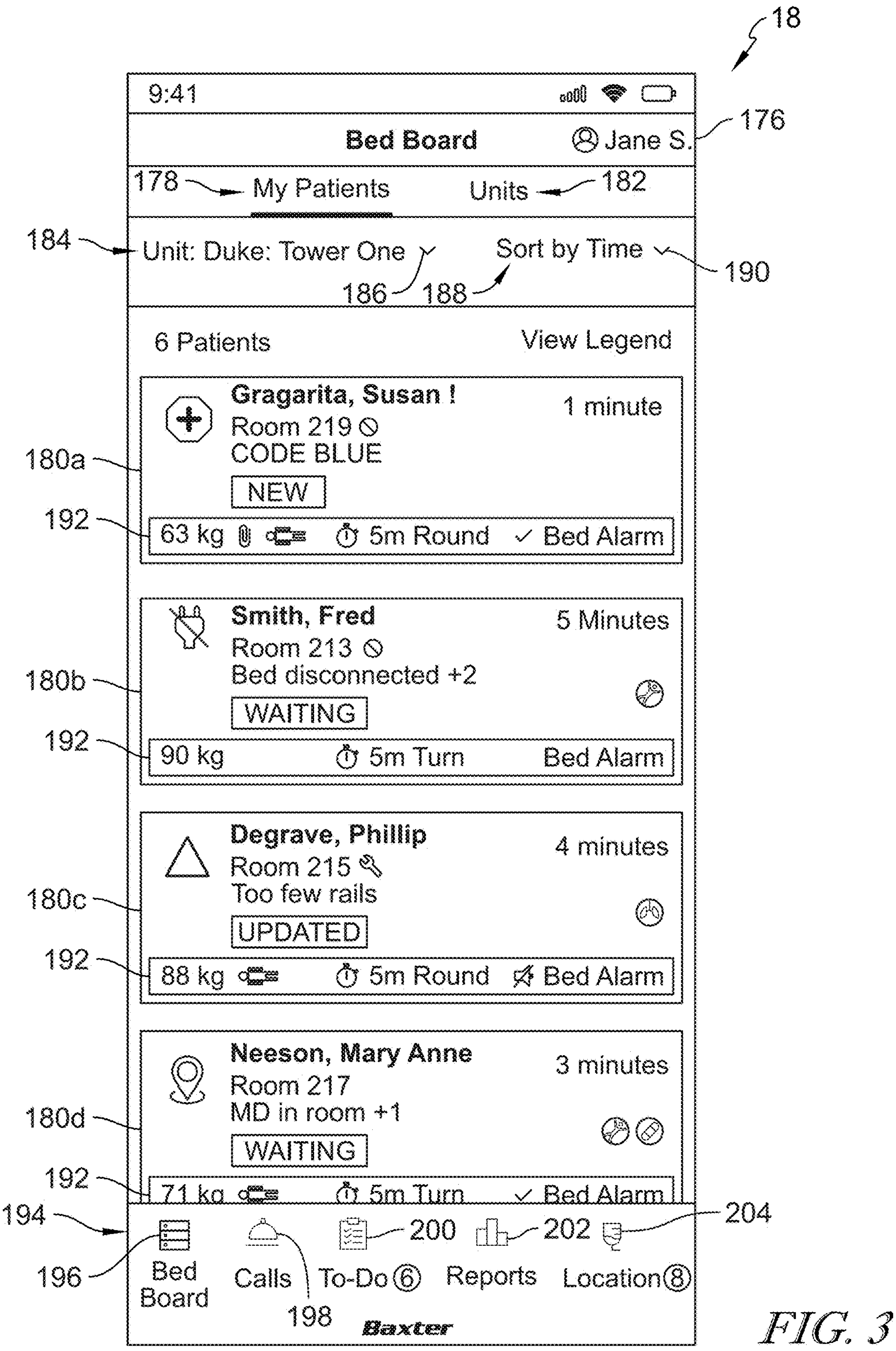
FIG. 3 is a bed board screen shot of the mobile phone of FIG. 1 showing a list of patient calls and alerts sorted by time of occurrence.

Referring now to FIG. 3, an example of a bed board screen shot 176 which appears on the display of the mobile phone 18 is shown. The information shown in screen shot 176 is based on selection of a My Patients button 178 near the top of screen shot 176. Thus, the information shown in screen shot 176 is associated with the patients that have been assigned to the particular caregiver in possession of the corresponding mobile phone 18. As shown on screen shot 176, windows 180*a*, 180*b*, 180*c*, 180*d* are provided for four of the caregiver's six assigned patients. To see the information for the other two patients assigned to the caregiver, the caregiver simply swipes upwardly or downwardly on the display of mobile phone 18, as appropriate. If a Unit button 182 is selected by the caregiver in lieu of My Patients button 178 then additional windows, similar to windows 180*a*, 180*b*, 180*c*, 180*d*, are viewable on the display of mobile phone 18 for the additional patients in the unit, and the caregiver swipes upwardly or downwardly on the display of mobile phone 18, as appropriate, to see the information for the other patients in the unit.

Beneath the My Patients button 178 a text string 184 is provided on screen 176 indicating that the caregiver's unit is "Duke: Tower One." A drop down menu arrow 186 is situated adjacent to text string 184 and is selectable to bring up a drop down menu of other units of the caregiver's healthcare facility. Selection of a different unit results in the caregiver's assigned patient list and unit patient list to be updated, as appropriate (e.g., the caregiver may not have any assigned patients in other units). Beneath the Units button 182 is a text string 188 which states "Sort by Time" to indicate that the list of patients is sorted by the time since an alarm occurred or a call was other detected or placed. However, as shown in window 180*a*, a code blue call takes precedence over all other calls regardless of time since occurrence. For other calls, they are listed such that the oldest call is first, the second oldest call is second, and so on. In screen shot 176, window 180*b* shows a wait time of 5 minutes, window 180*c* shows a wait time of 4 minutes, and window 180*d* shows a wait time of three minutes. The wait times are shown in the upper right corner regions of windows 180*a*, 180*b*, 180*c*, 180*d*.

Next to text string 188 is a drop down menu arrow 190 which is selectable to sort the My Patients list and the Units list in some other manner, such as alphabetically by patient name or in room number order. Selection of a different sort methodology results in the My Patients list and Units list being updated accordingly. Each of windows 180*a*, 180*b*, 180*c*, 180*d* includes each patient's full name, the room number for the respective patient, a text description of any alarms or alerts (these terms are used interchangeably herein), and any icons associated with the alarms or alerts. The icons match the icons appearing on the bed status board 136 for the particular alert or call. In window 180*d*, a locating icon is provided to indicate that a medical doctor (MD) is located in the corresponding patient room and the associated text indicates there is an additional person (i.e., "+1") in the room as well.

An indicator box is provided beneath the foregoing information to indicate with the call or alert is new, waiting, or updated. Each window 180*a*, 180*b*, 180*c*, 180*d* includes a field 192 at the bottom region thereof with information regarding, from left to right, the patient's weight, whether the patient is sensed as being in bed, any reminders (e.g., rounding reminders or turn reminders) and the amount of time before the reminded action is due, and whether any bed alarms for the corresponding patient are occurring. Risk icons for any patient risks of the corresponding patient are shown above the right side of fields 192. The risk icons match those appearing in column 144 of status board 136 in some embodiments. At the bottom screen 176 of FIG. 3, a menu 194 of navigation icons are provided. Menu 194 includes a bed board icon 196 which is shown to be the currently selected navigation icon, a calls icon 198 which is selected to navigate to calls information, a to do icon 200 which is selected to navigate to the associated caregiver's to do list, a reports icon 202 to navigate to various reports and staff metrics, and a location icon 204 to navigate to location information for the healthcare facility.

Based on the foregoing, it should be appreciated that the present disclosure contemplates that all information appearing on status board 136 is viewable on the mobile devices 18 assigned to the respective caregivers of the corresponding unit of the healthcare facility. For example, in some embodiments, the caregiver is able to tap within a selected window 180*a*, 180*b*, 180*c*, 180*d* to bring up more information from status board 136 regarding the corresponding patient for viewing on the display of the associated mobile phone 18. The present disclosure also contemplates that the caregivers can provide user inputs on their mobile phones 18 to add and remove notes from column 142; to designate and de-designate patient risks from column 144, thereby causing icons 146, 148, 150, as the case may be, to appear in column 144 for selected patients or to disappear from column 144 for selected patients; and to place staff calls and staff emergency calls which appear in column 158; and to indicate that calls appearing in column 158 have been taken care of and can be cleared from column 158.

Figure 4:
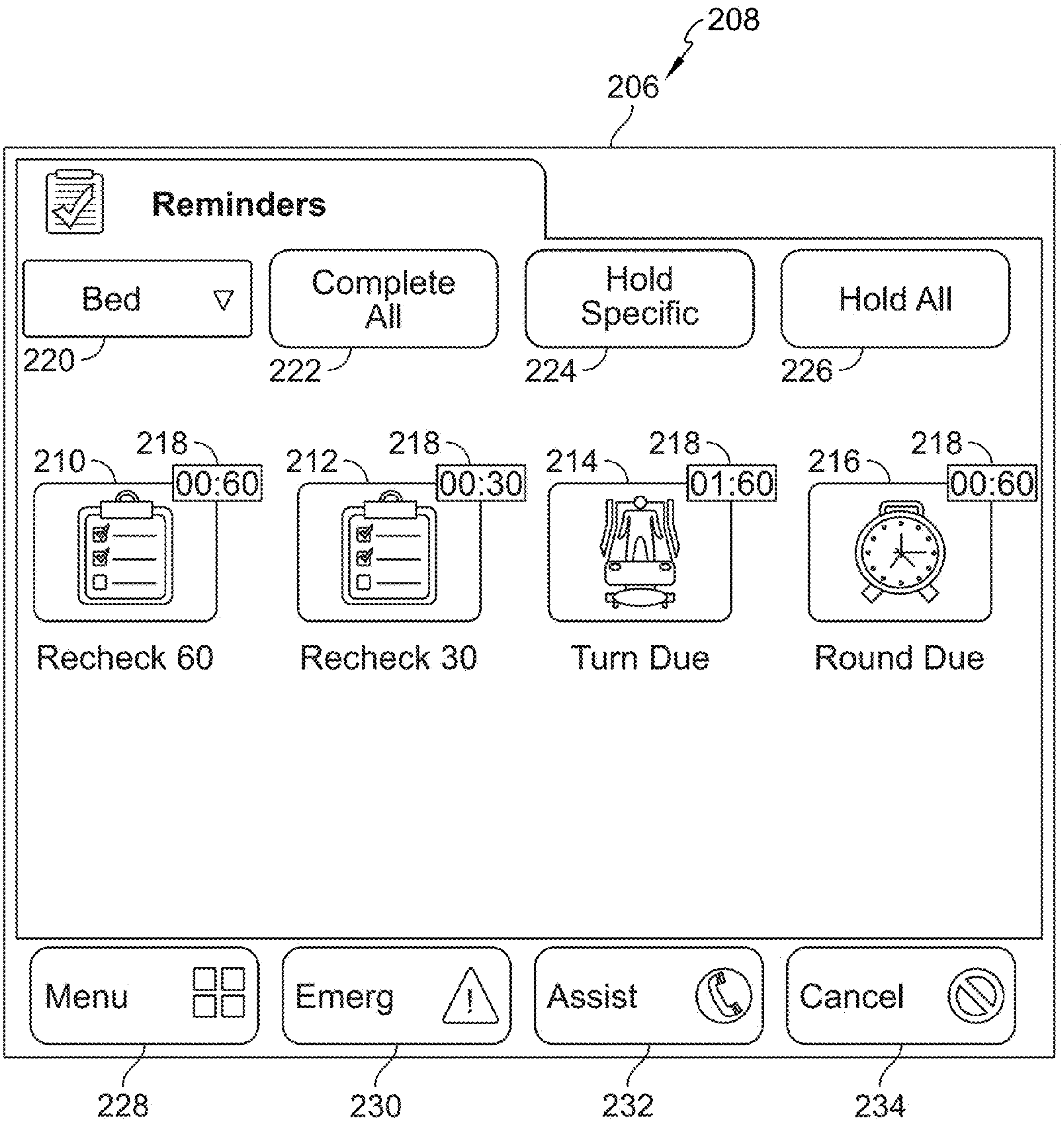
FIG. 4 is a reminders screen shot of a graphical room station (GRS) of the nurse call system of FIG. 1 showing a list of reminders or tasks that a caregiver is to perform for a patient in the room having the GRS.

Referring now to FIG. 4, a reminders screen shot of a graphical room station (GRS) 208 of the nurse call system 12 of FIG. 1 is show with a list of reminders or tasks, in the form of buttons, that an assigned caregiver is to perform for a patient in the room having the GRS 208. In the illustrative FIG. 4 example, screen shot 206 includes a 60-minute recheck reminder 210, a 30-minute recheck reminder 212, a turn due reminder 214, and a round due reminder 216. A timer 218 is provided at the upper right corner of reach reminder 210, 212, 214, 216 indicating the amount of time, in hours: minutes format, before the particular reminder or task is due. Thus, reminder 210 is due in 60 minutes, reminder 212 is due in 30 minutes, reminder 214 is due in one 1 hour and 60 minutes (aka 2 hours), and reminder 216 is due in 60 minutes.

After a caregiver completes the task associated with a particular reminder 210, 212, 214, 216, the caregiver selects the button or the particular reminder 210, 212, 214, 216 by touching or tapping the button on the display of the GRS 208 which clears the reminder from system 10 or provides a subsequent screen with an input for the caregiver to select to clear the reminder. Above the reminders 210, 212, 214, 216 on screen shot 206 are a bed button 220 which is selected to view reminders associated with the corresponding patient's bed, a complete all button 222 which is selected to clear all of the reminders 210, 212, 214, 216 as being completed by the caregiver, a hold specific button 224 which is selected to indicate that a particular one of reminders 210, 212, 214, 216 is to be paused from being completed, and a hold all button 226 which is selected to indicate that all of reminders 210, 212, 214, 216 are to be paused. When some or all of reminders 210, 212, 214, 216 are paused, the associated timer 218 ceases from continuing to count down during the pause period. If hold specific button 224 is selected, then the specific reminder 210, 212, 214, 216, as the case may be, is subsequently selected to indicate which specific reminder is to be paused.

At the bottom of screen shot 206, from left to right, are a menu button 228 which is selected to navigate to a main menu of the GRS 208, an emergency button 230 which is selected by a caregiver to summon other caregivers to come to the associated room due to an emergency (e.g., a combative or uncooperative patient), an assist button 232 which is selected by a caregiver to place a call to another staff member, and a cancel button 234 which is selected to cancel a call or alert that originated in the patient room in which the GRS 208 is fixed in place. The present disclosure contemplates that some or all of the features and functions concerning reminders 210, 212, 214, 216, 216 and buttons 220, 222, 224, 226, 228, 230, 232, 234 of GRS 208 are also able to be performed using mobile phones 18 of system 10.

Figure 5:
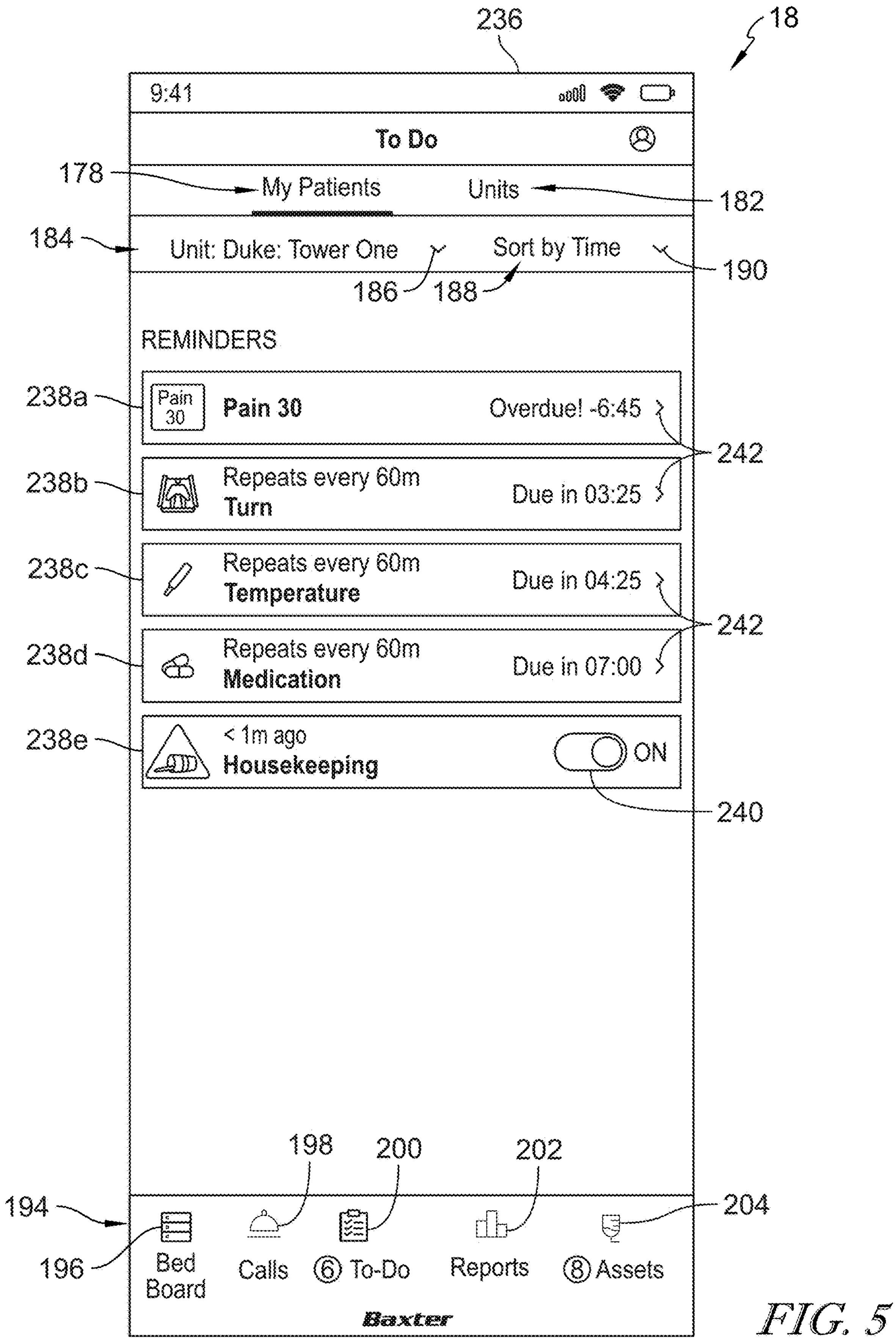
FIG. 5 is a to do screen shot of the mobile phone of FIG. 1 showing a list of reminders for the patients assigned to the caregiver associated with the mobile phone.

Referring now to FIG. 5, an example of a to do screen shot 236 of the mobile phones 18 of FIG. 1 is provided. Portions of screen shot 236 of FIG. 5 that are similar to like portions of screen shot 176 of FIG. 3 are denoted with like reference numbers and the descriptions are not repeated. As shown on screen shot 236, a list of reminders, in the form of windows 238*a*, 238*b*, 238*c*, 238*d*, 238*e*, are shown for the patients assigned to the caregiver associated with the mobile phone 18. In the example of FIG. 5, window 238*a* shows a pain reminder indicating that pain medication delivery is overdue by 6 minutes, 45 seconds (indicated by "–06:45); window 238*b* shows a turn reminder indicating that a corresponding patient's turn in bed is due in 3 minutes, 25 seconds (indicated by "03:25"); window 238*c* shows a temperature reminder indicating that a corresponding patient's temperature is to be taken in 4 minutes, 25 seconds (indicated by "04:25"); window 238*d* shows a medication reminder that is due in 7 minutes (indicated by "07:00"); and window 238*e* shows that housekeeping has been summoned to a corresponding patient room less than 1 minute ago.

Windows 238*b*, 238*c*, 238*d* have text above the reminder names to indicate that the corresponding task is a recurring task. In the illustrative example, the reminders of windows 238*b*, 238*c*, 238*d* each recur or repeat every 60 minutes. Window 238*e* includes a slider 240 that is selected to toggle between on and off positions to indicate whether housekeeping is needed in the corresponding patient room, when in the on position, or not needed in the corresponding patient room, when in the off position. As is apparent in the preceding paragraph, the time left before a particular task associated with a reminder is due is provided in minutes: seconds format, with a negative sign indicating that the particular task is overdue.

Each of windows 238*a*, 238*b*, 238*c*, 238*d* includes a right arrow icon 242 which is selectable to view more information (e.g., room number and patient name) regarding the particular reminder and to view user inputs, such as icons or buttons, for managing the respective reminders (e.g., clear the reminders, reset the reminders, and pause the reminders). In response to use of the user inputs of the mobile phones 18 by caregivers to clear, reset, or pause the reminders, messages are transmitted back through mobile app gateway 16 and/or CSA 14 to nurse call system 12 which updates status board 136 and GRS 208 accordingly. At the bottom of screen shot 236, to do icon 200 is highlighted to indicate that the to do information of the corresponding caregiver is to be provided on the display of mobile phone 18 (note that the bed board icon 196 should not be highlighted in FIG. 5).

Figure 6:
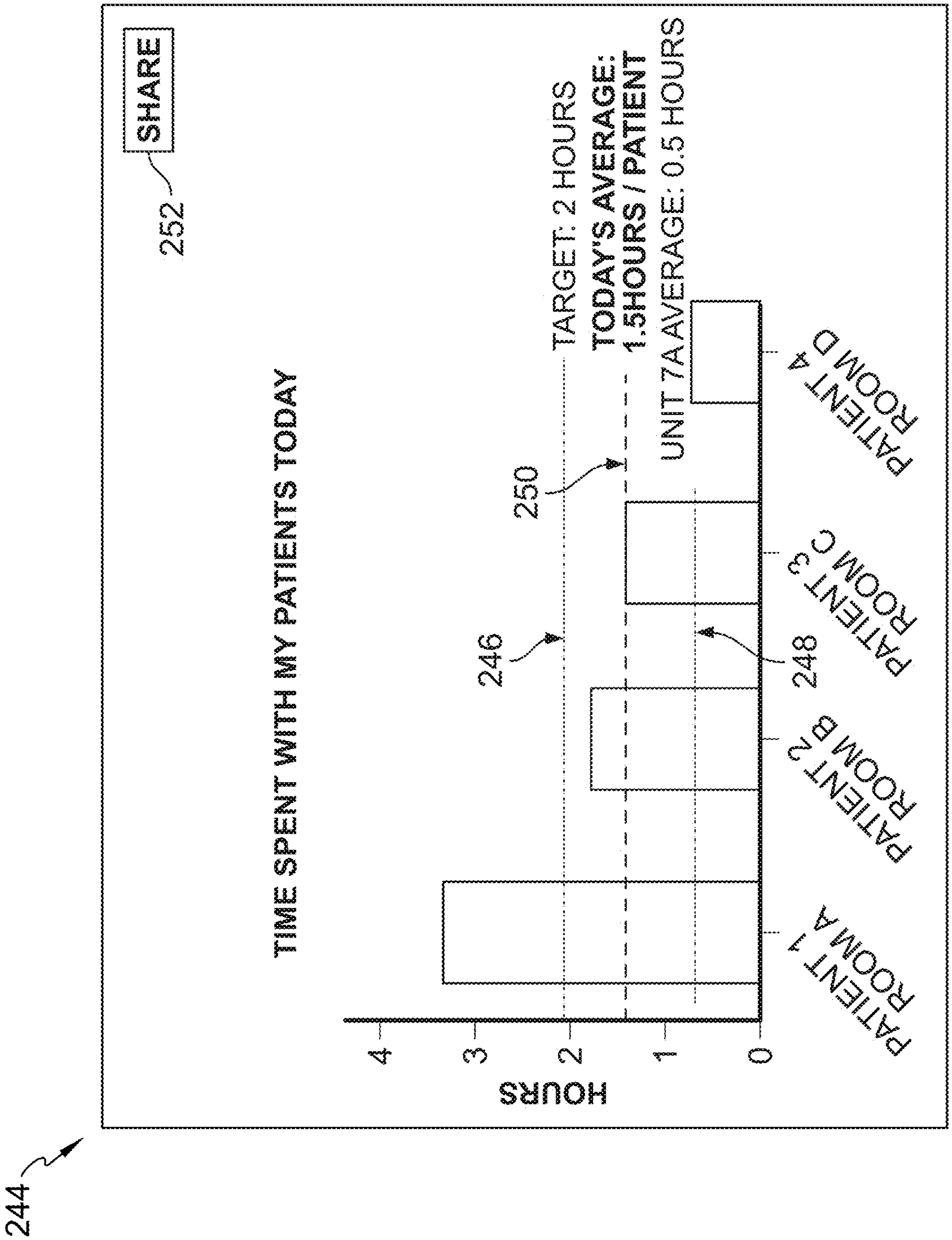
FIG. 6 is a caregiver metrics graph that is viewable on a screen of the mobile phone of the respective caregiver showing the amount of time that the respective caregiver has spent with each of the caregiver's assigned patients during the caregiver's shift.

Referring now to FIG. 6, an example is shown of a caregiver metrics graph 244 that is viewable on a screen of the mobile phone 18 of the respective caregiver in response to selection of reports button 202 of menu 194. Graph 244 is a bar graph showing the time in hours on the y-axis of the graph 244 that the caregiver spent with each of the caregiver's assigned patients during a particular shift. The bars of the bar graph 244 are shown generically as corresponding to Patient 1, Room A; Patient 2, Room B; Patient 3, Room C; and Patient 4, Room D along the x-axis. In an actual implementation, the names of the patients are shown in graph 244 (e.g., full patient name or HIPAA compliant version of patient name) along with the corresponding room number.

In graph 244, a first horizontal dotted line 246 shows the target amount of time that caregivers should endeavor to spend with each of their patients during a shift and a second horizontal dotted line 248 shows the average amount of time that caregivers in the unit spent with their assigned patient's during the shift. Also in graph 244, a dashed horizontal line 250 shows the average amount of time that the respective caregiver spent with the caregiver's assigned patients during the caregiver's shift. Graph 244 also includes, in the upper right corner region, a share button 252 for selection by the caregiver of the mobile phone 18 on which graph 244 is displayed to send a copy of the graph to other staff members.

Figure 7:
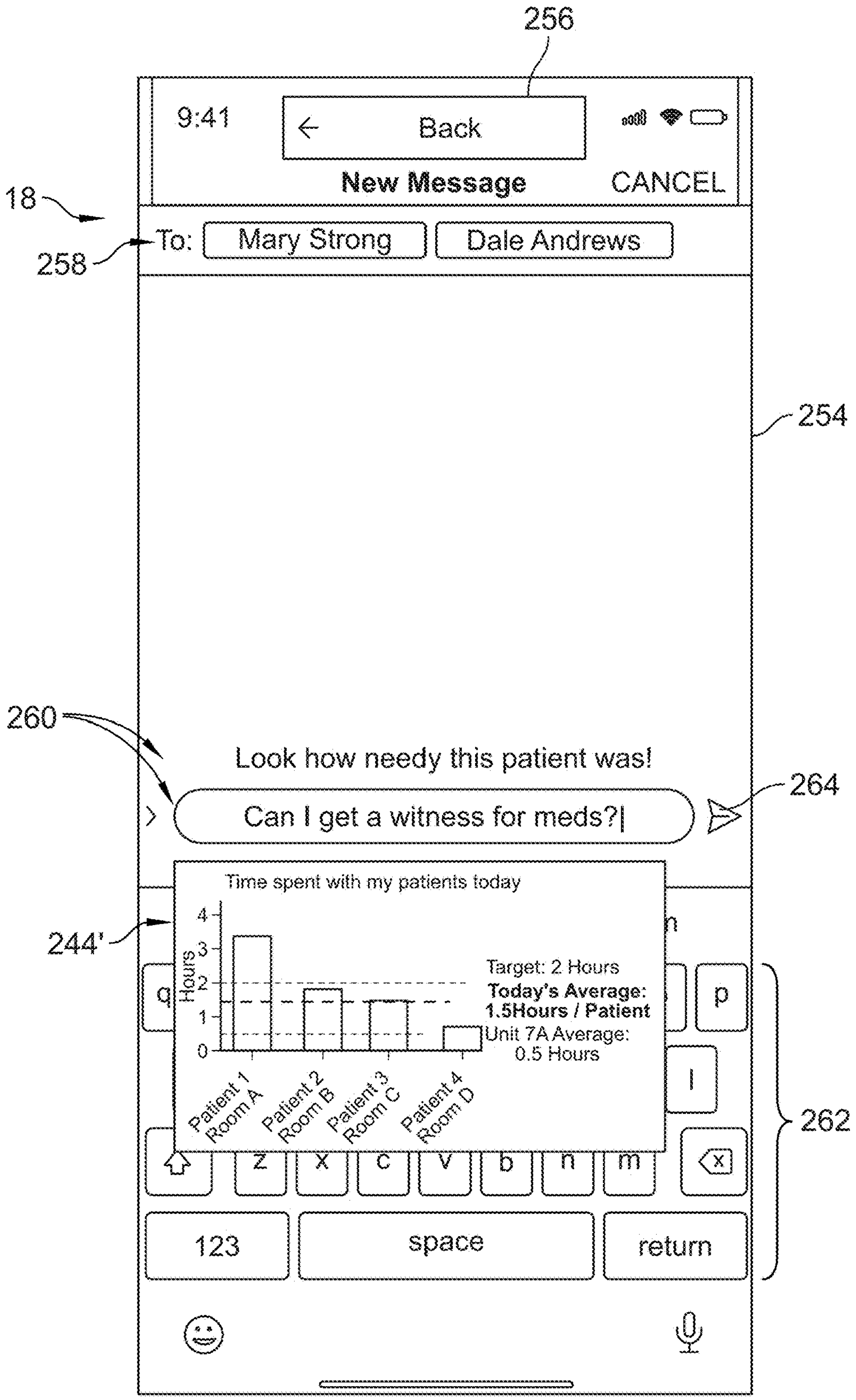
FIG. 7 is metrics screen shot of the mobile phone of FIG. 1 showing that the caregiver is able to share the caregiver's metrics graph with other staff after a share button, shown in FIG. 6, is selected.

Referring now to FIG. 7, an example of a share graph screen shot 254 is shown. Screen shot 254 appears on the touchscreen display of the respective caregiver's mobile phone 18 in response to selection of share button 252 of graph 244. As shown in FIG. 7, a duplicate graph 244' is displayed and contains the same information as graph 244 except that graph 244' does not include display button 252. The present disclosure contemplates that, in response to selection of share button 252, the caregiver's mobile phone 18 launches another application for sending secure text messages to other caregivers in the healthcare facility. An example of such an application is the VOALTE® communication application available from Hill-Rom Company, Inc. of Batesville, IN, U.S.A. At the top of screen shot 254 is a back button 256 the selection of which returns the caregiver back to the mobile application for linking the mobile phone 18 with nurse call system 12.

Beneath back button 256 of screen shot 254 is a text message recipient field 258 in which recipients of the text are listed. In the illustrative example, field 258 includes the text "To: Mary Strong Dale Andrews" to indicate that two recipients are to receive the text message having graph 244'. Just above graph 244' of screen shot 254 is a text message field 260, which in the illustrative example includes two lines of text. The first line of text is, "Look how needy this patient was!" and the second line of text is "Can I get a witness for meds?" A keyboard 262 is provided on the display of the caregiver's mobile phone 18 for use to type the text message(s) in field 260. Screen shot 254 also has a send arrow 264 to the right of field 260 for selection to send the text message(s) and graph 244' to the recipients listed in field 258.

Based on the foregoing, it will be appreciated that the present disclosure contemplates that mobile phones 18 of system 10 are usable for at least the following functionality, some of which have been discussed hereinabove: View patient, room, & bed data; Answer Nurse Calls; submit Action Requests (ARBs); handle Reminders (View, Pause, Reset, Complete); Staff Locator (from RTLS 34); Asset Locator (from RTLS 34); Interapp Linking such as to the VOALTE® communication application and EMR system linking; Updating Risks; Patient Safety Alerts (including toggling); and Shift metrics & reporting.

Additional details of the features and functionality of system 10 and particularly, the integration of mobile phones 18 with nurse call systems 12 of healthcare facilities is provided in Appendices 1, 2, and 3 of U.S. Provisional Application No. 63/617,143, filed Jan. 3, 2024, which is already incorporated by reference herein.

When terms of degree such as "generally," "substantially," and "about" are used herein in connection with a numerical value or a qualitative term susceptible to a numerical measurement, it is contemplated that an amount that is plus or minus 10 percent, and possibly up to plus or minus 20 percent, of the numerical value, is covered by such language, unless specifically noted otherwise, to at least account for manufacturing tolerances. Otherwise, a suitable definition for "generally," "substantially," and "about" is largely, but not necessarily wholly, the term specified.

When the terms "a" or "an" or the phrases "one or more" or "at least one" are used herein, including in the claims, they are all intended to be synonymous and mean that one or more than one of the thing recited may be present. Similarly, when the phrases "a plurality" or "two or more" or "at least two" or "a pair" are used, they are all intended to be synonymous and mean that two or more than two of the thing recited may be present.

According to this disclosure, phrases of the form "at least one of A and B" and "at least one of the following: A and B"

and similar such phrases, mean "A, or B, or both A and B." Phrases of the form "at least one of A or B" and "at least one of the following: A or B" and similar such phrases, also mean "A, or B, or both A and B."

Although certain illustrative embodiments have been described in detail above, variations and modifications exist within the scope and spirit of this disclosure as described and as defined in the following claims.

The invention claimed is:

1. A healthcare information system comprising a nurse call system located at a health care facility, the nurse call system including a nurse call server, a plurality of graphical room stations mounted in patient rooms of the healthcare facility and coupled to the nurse call server, and a status board communicatively coupled to the nurse call server, the nurse call server being configured to receive nurse calls, alerts, and device status data from devices located in the patient rooms of the healthcare facility, wherein the devices located in the patient rooms include patient beds that support patients in the patient rooms, the status board being configured to display at a master nurse station of a unit of the healthcare facility information pertaining to the nurse calls, alerts, and device status data, connected services architecture (CSA) located at an entity geographically remote from the healthcare facility, the CSA being communicatively coupled to the nurse call server and having a proxy server configured to replicate the nurse calls, alerts, and device status data communicated to the proxy server from the nurse call server, a mobile application gateway communicatively coupled to the nurse call server via a first path that excludes the proxy server of the CSA and via a second path that includes the proxy server of the CSA, and wireless mobile devices carried by caregivers in the healthcare facility and each wireless mobile device being communicatively coupled with the mobile application gateway, each wireless mobile device being configured to receive and display the nurse calls, alerts, and device status data from the mobile application gateway such that the wireless mobile devices have access to all of the information being displayed on the status board, and wherein each graphical room station of the plurality of graphical rooms stations is configured to permit caregivers, when in the patient room in which a respective graphical room station is mounted, to manually add and clear staff calls and staff emergency calls to and from, respectively, a staff calls column appearing on the status board, and wherein each of the wireless mobile devices carried by the caregivers is configured to permit the caregivers, when not in any of the patient rooms, to manually add and clear the staff calls and the staff emergency calls to and from, respectively, the staff calls column appearing on the status board.

2. The healthcare information system of claim 1, further comprising a master station computer communicatively coupled to the nurse call server and to the status board, and wherein the status board is configured to display, for each patient room in the unit, the associated nurse calls, alerts, and device status data in a table format.

3. The healthcare information system of claim 2, wherein the status board is configured to display, for each patient room in the unit, risk information pertaining to an associated patient in each of the patient rooms, the risk information being replicated in the proxy server of the CSA.

4. The healthcare information system of claim 3, wherein the risk information includes a first icon to indicate that the patient is a falls risk, a second icon to indicate that the patient is a pulmonary risk, and a third icon to indicate that the patient is at risk of developing pressure sores, and wherein each wireless mobile device is configured to receive inputs from an associated caregiver to designate a corresponding patient with one or more of being a falls risk, being a pulmonary risk, and being at risk of developing pressure sores.

5. The healthcare information system of claim 3, wherein each wireless mobile device is configured to control the display of the risk information on the status board based on inputs received from an associated caregiver to designate whether or not a corresponding patient has a particular risk.

6. The healthcare information system of claim 1, wherein each wireless mobile device is configured to display a list of nurse calls and alerts for patients or patient rooms assigned to the associated caregiver.

7. The healthcare information system of claim 6, wherein the list of nurse calls and alerts are sorted based on time since occurrence, with a most recent nurse call or alert being listed first.

8. The healthcare information system of claim 6, wherein the list includes, for each nurse call or alert, a field that includes the associated patient name, the associated room, a description of the associated type of nurse call or alert, and a time since the nurse call or alert occurred.

9. The healthcare information system of claim 8, wherein the list includes, for each nurse call or alert, an icon indicative of the associated type of nurse call or alert.

10. The healthcare information system of claim 6, wherein the list includes, for each nurse call or alert, reminder information including at least one of the following: a rounding reminder if the associated caregiver is scheduled to make a round for the corresponding patient or a turn reminder if the associated caregiver is scheduled to turn the associated patient.

11. The healthcare information system of claim 1, wherein the plurality of graphical room stations are configured to display reminder information pertaining to tasks that are to be completed by caregivers for the patients in the respective rooms, and wherein the wireless mobile devices are configured to receive one or more inputs from the associated caregivers indicative of completion of the tasks.

12. The healthcare information system of claim 11, wherein the reminder information comprises rounding reminders and the one or more inputs indicate that the associated caregiver has completed a round for a corresponding patient.

13. The healthcare information system of claim 11, wherein the reminder information comprises turn reminders and the one or more inputs indicate that the associated caregiver has completed a turn of the corresponding patient.

14. The healthcare information system of claim 11, wherein the reminder information comprises medication reminders and the one or more inputs indicate that the associated caregiver has completed medication delivery to the corresponding patient.

15. The healthcare information system of claim 11, wherein the reminder information comprises patient temperature reminders and the one or more inputs indicate that the associated caregiver has completed taking the corresponding patient's temperature.

16. The healthcare information system of claim 11, wherein selection of the one or more inputs by the caregivers to indicate completion of the tasks are communicated to the nurse call server resulting in task lists for the caregivers being updated.

17. The healthcare information system of claim 1, wherein the wireless mobile devices are configured with an input to summon housekeeping personnel to a selected patient room.

18. The healthcare information system of claim 1, wherein the nurse call server tracks caregiver performance metrics for each caregiver and wherein the wireless mobile devices are configured to display the caregiver performance metrics for the associated caregiver.

19. The healthcare information system of claim 18, wherein the caregiver performance metrics comprise a time spent with each of the associated caregiver's assigned patients during a particular shift.

20. The healthcare information system of claim 1, wherein the wireless mobile devices are configured to display one or more call completion inputs that are selectable by the associated caregiver to notify the nurse call server that a particular nurse call has been answered or that a particular alert condition has been rectified.

21. The healthcare information system of claim 1, further comprising a locating system server communicatively coupled to the nurse call server and receiving locating data regarding locations of locating tags worn by caregivers and/or coupled to equipment in the healthcare facility, wherein the locating data is replicated in the proxy server of the CSA.

22. The healthcare information system of claim 21, wherein each of the wireless mobile devices is configured to display a floor plan of a portion of the healthcare facility and wherein locations of caregivers and/or equipment are shown on the floor plan based on the locating data.

23. The healthcare information system of claim 1, wherein each of the wireless mobile devices are configured to open a voice communication channel to a graphical room station located in an associated patient room from which a corresponding nurse call originated.

* * * * *